United States Patent [19]

Dohara et al.

[11] Patent Number: 5,190,745
[45] Date of Patent: Mar. 2, 1993

[54] INSECTICIDAL COMPOSITIONS

[75] Inventors: Kazunobu Dohara, Hirakata; Mitsuyasu Makita, Nishinomiya; Yasuo Abe, Toyonaka, all of Japan

[73] Assignee: Sumitomo Chemical Company, Limited, Osaka, Japan

[21] Appl. No.: 856,557

[22] Filed: Mar. 24, 1992

Related U.S. Application Data

[63] Continuation-in-part of Ser. No. 689,472, Apr. 23, 1991, abandoned.

[30] Foreign Application Priority Data

Apr. 24, 1990 [JP] Japan .................. 2-109840
Oct. 15, 1991 [JP] Japan .................. 3-266044

[51] Int. Cl.$^5$ ................ A61L 9/04; A01N 43/50
[52] U.S. Cl. ..................... 424/45; 514/389
[58] Field of Search .................. 514/389; 424/45

[56] References Cited

U.S. PATENT DOCUMENTS 4,176,189 11/1979 Itaya et al. ............. 514/389
4,295,581 10/1981 Yamaguchi et al. .......... 222/192

FOREIGN PATENT DOCUMENTS

| | | |
|---|---|---|
| 0045424 | 2/1982 | European Pat. Off. . |
| 0148625 | 7/1985 | European Pat. Off. . |
| 2738878 | 9/1978 | Fed. Rep. of Germany . |
| 3317823 | 11/1984 | Fed. Rep. of Germany . |
| 48-99337 | 12/1973 | Japan . |
| 53-72821 | 6/1978 | Japan . |
| 57-56405 | 4/1982 | Japan . |
| 2002635 | 7/1978 | United Kingdom . |
| 2224654 | 10/1989 | United Kingdom . |

*Primary Examiner*—Allen J. Robinson
*Attorney, Agent, or Firm*—Stevens, Davis, Miller & Mosher

[57] ABSTRACT

The insecticidal composition of the present invention contains (a) 2,4-dioxo-1-(2-propynyl)-imidazolidin-3-ylmethyl chrysanthemate and (b) at least one carboxylic acid ester selected from the group consisting of monocarboxylic acid ester having 16 to 19 carbon atoms and dicarboxylic acid ester having 16 to 19 carbon atoms, the weight ratio of (a) to (b) being from 3:1 to 1:100.

6 Claims, No Drawings

INSECTICIDAL COMPOSITIONS

CROSS-REFERENCE TO RELATED APPLICATIONS

This is a continuation-in-part application of Ser. No. 07/689,472, filed on Apr. 23, 1991, now abandoned.

The present invention relates to an insecticidal composition 2,4-Dioxo-1-(2-propynyl)imidazolidin-3-ylmethyl chrysanthemate having the formula (hereinafter Compound A),

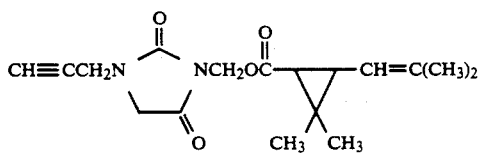

is a compound disclosed in U.S. Pat. No. 4,176,189, and is known to be usable as an active ingredient for insecticides. However, the compound does not exhibit a satisfactorily high insecticidal activity when used alone.

The present inventors have extensively studied to strengthen the insecticidal activity of Compound A, and as a result have found that when (b) at least one carboxylic acid ester selected from the group consisting of monocarboxylic acid esters having 16 to 19 carbon atoms and dicarboxylic acid esters having 16 to 19 carbon atoms is added to (a) Compound A so that the weight ratio of (a) to (b) is from 3:1 to 1:100, the insecticidal activity of Compound A is remarkably strengthened.

Furthermore, the inventors have found that the aerosol composition comprising Compound A, the carboxylic acid ester described above, kerosene, dimethyl ether (DME) and optionally liquefied petroleum gas (LPG) has a strengthened insecticidal activity.

According to the present invention, there is provided an insecticidal composition comprising:

(a) 2,4-dioxo-1-(2-propynyl)imidazolidin-3-ylmethyl chrysanthemate (Compound A), (b) at least one member selected from the group consisting of monocarboxylic acid esters having 16 to 19 carbon atoms and dicarboxylic acid esters having 16 to 19 carbon atoms, the weight ratio of (a) to (b) being from 3:1 to 1:100, and optionally (c) at least one inert carrier.

A preferred embodiment of the present composition is the aerosol composition comprising kerosene, DME and optionally LPG as an inert carrier.

Compound A includes various optical and geometrical isomers. Of the isomers, an isomer exhibiting an insecticidal activity and the mixtures thereof can be incorporated in the insecticidal composition of the present invention. The content of Compound A in the composition of the present invention is usually 0.001% to 75% by weight.

Specific examples of the monocarboxylic acid esters having 16 to 19 carbon atoms and the dicarboxylic acid esters having 16 to 19 carbon atoms are dibutyl phthalate, isopropyl palmitate, isopropyl myristate, hexyl laurate, etc. These compounds may also be used in admixture thereof. One of more compounds selected out of these compounds are usually blended in the composition of the present invention in an amount of 0.0003% to 75% by weight.

The aerosol composition, which is a preferred embodiment, usually comprises (a) 0.001 to 5% by weight of Compound A, (b) 0.005 to 60% by weight of the carboxylic acid ester, (c) 5 to 80% by weight of kerosene and (d) 20 to 80% by weight of a propellant which is DME or a mixture of DME and LPG.

Into the composition of the present invention may be incorporated one or more of other insecticides, (RS)-3-allyl-2-methyl-4-oxocyclopent-2-enyl (1RS)-cis,trans-chrysanthemate [allethrin];

3,4,5,6-tetrahydrophthalimidomethyl (1RS)-cis, trans-chrysanthemate [tetramethrin];

(S)-2-methyl-4-oxo-3-(2-propenyl)cyclopent-2-enyl (1R)-cis,trans-chrysanthemate [prallethrin];

3-phenoxybenzyl (1RS)-cis,trans-chrysanthemate [phenothrin];

5-benzyl-3-furylmethyl (1RS)-cis,trans chrysanthemate [resmethrin];

(RS)-α-cyano-3-phenoxybenzyl (1R)-cis,transchrysanthemate [cyphenothrin];

3-phenoxybenzyl (1RS)-cis,trans-3-(2,2-dichlorovinyl)-2,2-dimethylcyclopropanecarboxylate [permethrin];

(RS)-α-cyano-3-phenoxybenzyl (1RS)-cis,trans-3-(2,2-dichlorovinyl)-2,2-dimethylcyclopropanecarboxylate [cypermethrin];

(S)-α-cyano-3-phenoxybenzyl (1R)-cis-3-(2,2-dibromovinyl)-2,2-dimethylcyclopropanecarboxylate [deltamethrin];

(RS)-α-cyano-4-fluoro-3-phenoxybenzyl (1RS) -cis,-trans-3-(2,2-dichlorovinyl)-2,2-dimethylcyclopropanecarboxylate [cyfluthrin];

5-(2-propynyl)furfuryl (1RS)-cis,transchrysanthemate [furamethrin];

2-(4-ethoxyphenyl)-2-methylpropyl 3-phenoxybenzyl ether [ethofenprox];

2,3,5,6 -tetrafluorobenzyl (1R)-trans-(2,2-dichlorovinyl)-2,2-dimethylcyclopropanecarboxylate [benfluthrin];

2,2-dichlorovinyl dimethyl phosphate [dichlorvos];

O,O-dimethyl O-(3-methyl-4-nitrophenyl)-phosphorothioate [fenitrothion];

2-(1-methyethoxy)phenyl N-methylcarbamate [propoxur];

4-phenoxyphenyl (RS)-2-(2-pyridyloxy)propyl ether [pyriproxyfen];

isopropyl (2E,4E)-11-methoxy-3,7,11-trimethyl-2,4-dodecadienoate [methoprene];

ethyl (2E,4E)-3,7,11-trimethyldodeca-2,4-dienoate [hydroprene];

1-(4-chlorophenyl)-3-(2,6-difluorobenzoyl)urea [diflubenzuron]; and

N-cyclopropyl-1,3,5-triazine-2,4,6-triamine [cyromazine].

Specific examples of the synergists are α-[2-(2-butoxyethoxy)ethoxy]-4,5-methylenedioxy-2-propyltoluene (piperonyl butoxide), N-(2-ethylhexyl)bicyclo[2,2,1-]hept-5-ene-2,3-dicarboximide (MGK-264), octachlorodipropyl ether (S-421), etc.

Specific examples of the solvents are isopropyl alcohol, kerosene, dodecylbenzene, etc.

Specific examples of the propellants are propane/butane, dimethyl ether, Freon TM gas (fluorocarbons), etc.

The composition of the present invention is prepared, for example, by mixing a prescribed amount of Compound A and a prescribed amount of at least one carboxylic acid ester described above, and if necessary other insecticides, synergists, perfumes, fungicides, solvents, propellants, solid carriers, etc. at room temperature or under heating.

And an aerosol composition is prepared, for example, by putting the mixture obtained above in an aerosol can, mounting a valve portion on the can and charging a propellant into the can under pressure through the valve portion.

Insects and acarina against which the composition of the present invention thus prepared is effective are listed below:

Lepidoptera casemaking clothes moth (*Tinea pellionella*), webbing clothes moth (*Tineola bisselliella*), etc.

Diptera

*Culex* spp. such as common mosquito (*Culex pipiens pallens*) and *Culex tritaeniorhynchus:* Aedes spp. such as *Aedes aeovoti:* and *Aedes albopictus; Anopheles* spp. such as *Anopheles sinensis:* midges (Chironomidae); Muscidae such as housefly (*Musca domestica*) and false stablefly (*Muscina stabulans*); Calliphoridae; Sarcophagidae; little housefly (*Fannia canicularis*); Anthomyiidae such as seedcorn maggot (*Delia platura*) and onion maggot (*Delia antiqua*); fruit flies (Tephritidae); Drosophilidae; moth flies (Psychodidae); black flies (Simuliidae); Tabanidae, stable flies (Stomoxyidae) etc.

Dictyoptera

German cockroach (*Blattella germanica*), smoky-brown cockroach (*Periplaneta fuliginosa*), American cockroach (*Periplaneta americana*), brown cockroach (*Periplaneta brunnea*), oriental cockroach (*Blatta orientalis*), lobster cockroach (*Nauphoeta cinerea*), harlequin cockroach (*Neocylopyga rhombifolia*), Japanese cockroach (*Periplaneta japonica*), Australian cockroach (*Periplaneta australasiae*), etc.

Hymenoptera ants (Formicidae), hornets (Vespidae), Bethylidae, sawflies (Tenthredinidae) such as cabbage sawfly (*Athalia rosae rufincornis*), etc.

Siphonaptera human flea (*Pulex irritans*), dog flea (*Ctenocephalides canis*), cat flea (*Ctenocephalides felis*), oriental rat flea (*Xenopsylla cheopis*), etc.

Isoptera

*Reticulitermes speratus, Coptotermes formosanus* etc.

Ixodidae

*Boophilus microplus,* etc.

House Dust Mites

Acaridae such as *Tyrophaqus putrescentiae,* Pyroalyphidae such as *Dermatophagoides farinae,* Cheyletidae such as *Chelacaropsis moorei,* Macronyssidae such as *Ornithonyssus bacoti,* etc.

The composition of the present invention is especially useful for controlling cockroaches. Although many pesticides for cockroaches are on sale, consumers cannot confirm the effect of such conventional pesticides because cockroaches run away and hide themselves quickly. In contrast, the composition of the present invention has an excellent knock-down effect so that consumers can easily confirm the result and dispose the bodies.

The composition of the present invention can be used as it is for killing the insect pests; however, it is usually used formulated into the form of preparation such as aerosols, oil sprays, etc.

The aerosol composition of the present invention usually contains 0.001 to 5% by weight, preferably 0.05 to 2% by weight, of Compound A and 0.05 to 60% by weight, preferably 0.1 to 40% by weight of the carboxylic acid ester described above.

Any kerosene used for insecticidal aerosols can be available for the present aerosol composition. The examples of kerosene are n-paraffin type such as NEO-CHIOZOL ® (manufactured by Chuokasei Company), isoparaffin type such as ISOPAR ®G, ISOPAR ®H ISOPAR ®M (manufactured by Exxon Chemical Company), IP-2028 (manufactured by Idemitsu Sekiyu Kagaku Company) and the mixtures thereof. The content of the kerosene is 5 to 80% by weight, preferably 30 to 70% by weight in the aerosol composition.

DME or a mixture of DME and LPG is preferable for the present aerosol composition as a propellant. The mixing ratio of DME and LPG is usually 100:0 to 40:60 by weight. The content of the propellant ranges 20 to 80% by weight, preferrably 30 to 70% by weight in the aerosol composition.

Into the aerosol composition may be incorporated one or more of other insecticides and synergists.

The content of the other insecticide is at mos 3%, preferably 2% by weight in the composition and the content of the synergist is at most 4%, preferably 2% by weight in the composition.

The present invention is illustrated in more detail with reference to the following Examples, Comparative Examples and Test Examples; however, the present invention should not be interpreted as being limited thereto.

In Examples, Comparative Examples and Test Examples, parts are by weight.

EXAMPLE 1

50.0 Parts of Compound A (acid moiety: d-trans configuration) and 50.0 parts of isopropyl myristate were mixed under heating (about 40° to 50° C.) to obtain a liquid insecticidal composition.

Table 1 lists the insecticidal compositions obtained in the same manner as above.

TABLE 1

| | | Composition (part by weight) | | | | | | |
|---|---|---|---|---|---|---|---|---|
| | Compound A (acid moiety: d-trans configuration) | Carboxylic acid ester | | | | | | |
| | | Isopropyl myristate | Isopropyl palmitate | Hexyl laurate | Dibutyl phthalate | Diisopropyl adipate | Butyl stearate | Ethyl acetate |
| Example 1 | 1 | 99 | 0 | 0 | 0 | 0 | 0 | 0 |
| 2 | 10 | 90 | 0 | 0 | 0 | 0 | 0 | 0 |
| 3 | 50 | 50 | 0 | 0 | 0 | 0 | 0 | 0 |

TABLE 1-continued

| | | Composition (part by weight) | | | | | | |
|---|---|---|---|---|---|---|---|---|
| | Compound A | Carboxylic acid ester | | | | | | |
| | (acid moiety: d-trans configuration) | Isopropyl myristate | Isopropyl palmitate | Hexyl laurate | Dibutyl phthalate | Diiso-propyl adipate | Butyl stearate | Ethyl acetate |
| | 4 | 70 | 30 | 0 | 0 | 0 | 0 | 0 | 0 |
| | 5 | 50 | 0 | 50 | 0 | 0 | 0 | 0 | 0 |
| | 6 | 50 | 0 | 0 | 50 | 0 | 0 | 0 | 0 |
| | 7 | 50 | 0 | 0 | 0 | 50 | 0 | 0 | 0 |
| Com- | 1 | 100 | 0 | 0 | 0 | 0 | 0 | 0 | 0 |
| parative | 2 | 50 | 0 | 0 | 0 | 0 | 50 | 0 | 0 |
| Example | 3 | 50 | 0 | 0 | 0 | 0 | 0 | 50 | 0 |
| | 4 | 50 | 0 | 0 | 0 | 0 | 0 | 0 | 50 |

TEST EXAMPLE 1

Each of the insecticidal compositions obtained in Examples 1 to 7 and Comparative Examples 1 to 4 was diluted with acetone to obtain a solution containing 0.189 g/l of Compound A. 0.3 Milliliter of the solution was coated onto a petri dish of 8.5 cm in diameter so that Compound A was attached to the petri dish in an amount of 0.0567 mg. That is, Compound A was attached to the petri dish in a ratio of 10 mg/m$^2$. After the petri dish had been dried by evaporation of acetone, 10 German cockroaches (*Blattella germanica*) were released therein. The knock-down effect, KT$_{50}$ (the time required for knocking down 50% of the cockroaches) was determined. Table 2 shows the results.

TABLE 2

| | | KT$_{50}$ (min) to German cockroach |
|---|---|---|
| Example | 1 | 0.8 |
| | 2 | 0.9 |
| | 3 | 1.0 |
| | 4 | 0.9 |
| | 5 | 1.1 |
| | 6 | 0.9 |
| | 7 | 1.2 |
| Comparative Example | 1 | 3.0 |
| | 2 | 2.8 |
| | 3 | 4.1 |
| | 4 | 3.3 |

EXAMPLE 8

0.5 Part of Compound A, 0.5 part of isopropyl myristate, 45 parts of NEO-CHIOZOL ® and 14 parts of ISOPAR ®G were charged in a container. A valve was provided to the container. Forty parts of a propellant mixture of DME and LPG (the mixing ratio was 90:10 by weight) was filled through the valve into the insecticidal composition to obtain an aerosol.

EXAMPLE 9

0.5 Part of Compound A, 0.5 part of isopropyl myristate and 59 parts of NEO-CHIOZOL ® were charged in a container. A valve was provided to the container. Forty parts of a propellant mixture of DME and LPG (the mixing ratio was 75:25 by weight) was filled through the valve into the insecticidal composition to obtain an aerosol.

EXAMPLE 10

0.5 Part of Compound A, 0.5 part of isopropyl myristate and 59 parts of NEO-CHIOZOL ® were charged in a container. A valve was provided to the container. Forty parts of a propellant mixture of DME and LPG (the mixing ratio was 50:50 by weight) was filled through the valve into the insecticidal composition to obtain an aerosol.

EXAMPLE 11

0 5 Part of Compound A and 30.5 parts of isopropyl myristate were dissolved in 29 parts of NEO-CHIOZOL ®. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 12

Two parts of Compound A and 32 parts of isopropyl myristate were dissolved in 26 parts of NEO-CHIOZOL ®. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 13

0.1 Part of Compound A, 2 parts of tetramethrin and 30.1 parts of isopropyl myristate were dissolved in 27.8 parts of ISOPAR ®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 14

0.1 Part of Compound A, 1.0 part of (RS)-3-allyl-2-methyl-4-oxocyclopent-2-enyl (1RS)-cis,-trans(c:t=20:80)-chrysanthemate, 0.1 part of isopropyl myristate and 58.8 parts of ISORAR ®G were charged in a container. A valve was provided to the container. Forty parts of a propellant mixture of DME and LPG (the mixing ratio wa 50:50 by weight) was filled through the valve into the insecticidal composition to obtain an aerosol.

EXAMPLE 15

0.1 Part of Compound A, 0.1 part of prallethrin, 0.1 part of isopropyl myristate and 59.7 parts of ISOPAR ®M were charged in a container. A valve was provided to the container. Forty parts of a propellant mixture of DME and LPG (the mixing ratio was 50:50 by weight) was filled through the valve into the insecticidal composition to obtain an aerosol.

EXAMPLE 16

0.1 Part of Compound A, 0.1 part of d-phenothrin, 0.1 part of isopropyl myristate and 59.7 parts of IP-2028 were charged in a container. A valve was provided to the container. Forty parts of a propellant mixture of DME and LPG (the mixing ratio was 50:50 by weight) was filled through the valve into the insecticidal composition to obtain an aerosol.

EXAMPLE 17

0.1 Part of Compound A, 0.3 part of cyphenothrin, 0.1 part of isopropyl myristate and 59.5 parts of ISOPAR®M were charged in a container. A valve was provided to the container. Forty parts of a propellant mixture of DME and LPG (the mixing ratio was 50:50 by weight) was filled through the valve into the insecticidal composition to obtain an aerosol.

EXAMPLE 18

0.1 Part of Compound A, 0.3 part of cypermethrin 0.1 part of isopropyl myristate and 40 parts of dibutyl phthalate were dissolved in 19.5 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 19

0.1 Part of Compound A, 0.025 part of cyfluthrin, 0.1 part of isopropyl myristate and 40 parts of hexyl laurate were dissolved in 19.775 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 20

0.1 Part of Compound A, 0.3 part of ethofenprox, 0.1 part of isopropyl myristate and 40 parts of isopropyl palmitate were dissolved in 19.5 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 21

0.1 Part of Compound A, 0.5 part of dichlorvos and 30.1 parts of isopropyl myristate were dissolved in 29.3 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 22

0.1 Part of Compound A, 0.5 part of fenitrothion and 30.1 parts of isopropyl myristate were dissolved in 29.3 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 23

0.1 Part of Compound A, 0.5 part of propoxur and 30.1 parts of isopropyl myristate were dissolved in 29.3 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 24

0.1 Part of Compound A, 0.1 part of pyriproxyfen and 30.1 parts of isopropyl myristate were dissolved in 29.7 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

EXAMPLE 25

0.1 Part of Compound A, 0.1 part of methoprene and 30.1 parts of isopropyl myristate were dissolved in 39.7 parts of ISOPAR®M. The resulting mixture was charged in a container. A valve was provided to the container. Thirty parts of a propellant mixture of DME and LPG (the mixing ratio was 50:50 by weight) was filled through the valve into the insecticidal composition to obtain an aerosol.

EXAMPLE 26

0.1 Part of Compound A, 0.1 part of diflubenzron and 30.1 parts of isopropyl myristate were dissolved in 39.7 parts of ISOPAR®H. The resulting mixture was charged in a container. A valve was provided to the container. Thirty parts of a propellant (DME) was filled through the valve into the insecticidal composition to obtain an aerosol.

EXAMPLE 27

0.1 Part of Compound A, 0.1 part of Cyromazine and 30.1 parts of isopropyl myristate were dissolved in 39.7 parts of ISOPAR®M. The resulting mixture was charged in a container. A valve was provided to the container. Thirty parts of a propellant (DME) was filled through the valve into the insecticidal composition to obtain an aerosol.

EXAMPLE 28

0.1 Part of Compound A, 0.5 part of piperonyl butoxide, 0.1 part of isopropyl myristate and 29.3 parts of NEO-CHIOZOL® were dissolved in a container. A valve was provided to the container. Seventy parts of a propellant mixture of DME and LPG (the mixing ratio was 75:25 by weight) was filled through the valve into the insecticidal composition to obtain an aerosol.

EXAMPLE 29

0.1 Part of Compound A, 0.5 part of S-421, 0.1 part of isopropyl myristate and 29.3 parts of NEO-CHIOZOL® were charged in a container. A valve was provided to the container. Seventy parts of a propellant mixture of DME and LPG (the mixing ratio was 75:25 by weight) was filled through the valve into the insecticidal composition to obtain an aerosol.

EXAMPLE 30

0.1 Part of Compound A, 2 parts of MGK-264, 0.1 part of isopropyl myristate and 27.8 parts of NEO-CHIOZOL ® were charged in a container. A valve was provided to the container. Seventy parts of a propellant mixture of DME and LPG (the mixing ratio was 75:25 by weight) was filled through the valve into the insecticidal composition to obtain an aerosol.

EXAMPLE 31

0.1 Part of Compound A, 0.1 part of benfluthrin and 30.1 part of isopropyl myristate were dissolved in 39.7 parts of ISOPAR®M. The resulting mixture was charged in a container. A valve was provided to the container. Forty parts of a propellant mixture of DME and LPG (the mixing ratio was 50:50 by weight) was filled through the valve into the insecticidal composition to obtain an aerosol.

TEST EXAMPLE 2

Ten German cockroaches (five males and five females) were released in a cylindrical vessel (diameter:13 cm, height: 10 cm) having a net of 40 mesh wire at 1 cm from the bottom. The vessel was put into a glass cylinder (diameter: 20 cm, height: 60 cm). Then 0.4 g of an aerosol to be tested was sprayed onto the cockroaches and the glass cylinder was quickly covered up. Thirty seconds after spraying, the vessel was taken out from the glass cylinder. The number of the knocked down cockroaches was counted at 1, 2, 3, 5, 7, 10, 15 and 20 minutes after spraying. The time required for knock 50% of cockroaches down, $KT_{50}$ value, was calculated by Blis' Probit method. Table 3 showns the $KT_{50}$ values thus obtained.

TABLE 3

|  |  | $KT_{50}$ value (min) |
|---|---|---|
| Example | 8 | 1.7 |
|  | 9 | 1.7 |
|  | 10 | 1.7 |
|  | 11 | 1.9 |
|  | 12 | 0.8 |
|  | 13 | 3.5 |
|  | 14 | 3.3 |
|  | 15 | 3.4 |
|  | 16 | 3.4 |
|  | 17 | 3.0 |
|  | 18 | 3.8 |
|  | 19 | 3.9 |
|  | 20 | 4.0 |
|  | 21 | 3.4 |
|  | 22 | 4.0 |
|  | 23 | 3.9 |
|  | 24 | 3.4 |
|  | 25 | 3.6 |
|  | 26 | 3.8 |
|  | 27 | 3.8 |
|  | 28 | 4.9 |
|  | 29 | 4.7 |
|  | 30 | 5.0 |
|  | 31 | 4.5 |

Thereafter, all the cockroaches were put into another container and the mortality was checked after 3 days. Examples 7-11 and 16-22 showed 100% mortality.

The isomer of Compound A, the acid part of which is d-cis,trans (cis:trans=20:80), was used in Test Example 3.

TEST EXAMPLE 3

A plastic ring with butter applied on the inside was set in the center of a sheet having many concentric circle marks of 0.1 m to 1.4 m of radii. Ten German cockroaches or six American cockroaches were released in the ring. The aerosol obtained by Example 11 was sprayed directly one second for German cockroaches and three seconds for American cockroaches. The plastic ring was removed soon after spraying and the distance between the sprayed spot and the place the cockroaches were knocked down was measured. The cockroaches which were able to move more than 1.4 m were promptly collected.

The test was repeated 5 times and the median of the distances the cockroaches moved until knock-down were calculated. Table 4 shows the results.

The commercially available aerosols for cockroach (containing propoxur/dichlorvos or d-tetramethrin/permethrin as active ingredients) was subjected to the same test above. Table 4 also shows the results of these referential tests.

TABLE 4

| Active ingredient | | The distance (cm) | |
|---|---|---|---|
|  |  | German cockroach | American cockroach |
| Compound A | 0.5% | <10.0 | 17.2 |
| Propoxur | 2.0% | >140 | >140 |
| Dichlorvos | 0.5% |  |  |
| d-Tetramethrin | 0.6% | — | >140 |
| Permethrin | 0.5% |  |  |

What is claimed is:

1. An insecticidal aerosol composition which comprises:
   (a) 2,4-dioxo-1-(2-propynyl)imidazolidin-3-ylmethyl chrysanthemate,
   (b) at least one carboxylic acid ester selected from the group consisting of monocarboxylic acid esters having 16–19 carbon atoms and dicarboxylic acid esters having 16–19 carbon atoms,
   (c) kerosene, and
   (d) a propellant selected from the group consisting of dimethyl ether and a mixture of dimethyl ether and liquefied petroleum gas,
   the weight ratio of (a) to (b) being from 3:1 to 1:100.

2. An insecticidal aerosol composition according to claim 1, wherein the carboxylic acid ester is selected from the group consisting of dibutyl phthalate, isopropyl palmitate, isopropyl myristate and hexyl laurate.

3. An insecticidal aerosol composition according to claim 1, wherein the contents of (a), (b), (c) and (d) are 0.001 to 5% by weight, 0.005 to 60% by weight, 5 to 80% by weight and 20 to 80% by weight, respectively.

4. An insecticidal aerosol composition according to claim 3, wherein the weight ratio of dimethyl ether to liquefied petroleum gas is 100:0 to 40:60.

5. A method for controlling insects which comprises:
   applying to insects an insecticidal aerosol composition comprising:
   (a) 2,4-dioxo-1-(2-propynyl)imidazolidin-3-ylmethyl chrysanthemate,
   (b) at least one carboxylic acid ester selected from the group consisting of monocarboxylic acid esters having 16–19 carbon atoms and dicarboxylic acid esters having 16–19 carbon atoms,
   (c) kerosene, and
   (d) a propellant selected from the group consisting of dimethyl ether and a mixture of dimethyl ether and liquefied petroleum gas,
   the weight ratio of (a) to (b) being from 3:1 to 1:100.

6. A method according to claim 5, wherein the insects are cockroaches.